(12) United States Patent
Ziolo

(10) Patent No.: US 9,943,349 B2
(45) Date of Patent: Apr. 17, 2018

(54) ORTHOPEDIC DEVICES WITH A LOCKING MECHANISM

(71) Applicant: Blackstone Medical, Inc., Lewisville, TX (US)

(72) Inventor: Tara Ziolo, Hewitt, NJ (US)

(73) Assignee: Blackstone Medical, Inc., Lewisville, TX (US)

( * ) Notice: Subject to any disclaimer, the term of this patent is extended or adjusted under 35 U.S.C. 154(b) by 229 days.

(21) Appl. No.: 15/050,211

(22) Filed: Feb. 22, 2016

(65) Prior Publication Data

US 2016/0166295 A1   Jun. 16, 2016

Related U.S. Application Data

(62) Division of application No. 13/489,222, filed on Jun. 5, 2012, now Pat. No. 9,265,531.

(51) Int. Cl.
*A61B 17/80* (2006.01)
*A61B 17/70* (2006.01)

(52) U.S. Cl.
CPC ...... *A61B 17/8047* (2013.01); *A61B 17/7059* (2013.01); *A61B 17/8042* (2013.01)

(58) Field of Classification Search
None
See application file for complete search history.

(56) References Cited

U.S. PATENT DOCUMENTS

| | | | |
|---|---|---|---|
| 6,224,602 | B1 | 5/2001 | Hayes |
| 6,428,542 | B1 | 8/2002 | Michelson |
| 6,503,250 | B2 | 1/2003 | Paul |
| 6,652,525 | B1 | 11/2003 | Assaker et al. |
| 6,695,846 | B2 | 2/2004 | Richelsoph et al. |
| 6,755,833 | B1 | 6/2004 | Paul et al. |
| 7,438,715 | B2 | 10/2008 | Doubler et al. |
| 7,452,370 | B2 | 11/2008 | Anderson |
| 7,468,069 | B2 | 12/2008 | Baynham et al. |
| 7,488,321 | B2 | 2/2009 | Lin |
| 7,662,154 | B2 | 2/2010 | Ribeiro |
| 7,704,255 | B2 | 4/2010 | Michelson |
| 7,972,366 | B2 | 7/2011 | Richelsoph et al. |
| 8,016,864 | B2 | 9/2011 | Assaker et al. |
| 8,043,346 | B2 | 10/2011 | Markworth |
| 2004/0097935 | A1 | 5/2004 | Richelsoph et al. |
| 2004/0158246 | A1 | 8/2004 | Assaker et al. |
| 2004/0220571 | A1 | 11/2004 | Assaker et al. |
| 2005/0010227 | A1 | 1/2005 | Paul |

(Continued)

OTHER PUBLICATIONS

International Search Report and Written Opinion, PCT/US2013/043163, dated Aug. 15, 2013, 10 pages.

*Primary Examiner* — Sameh Boles
(74) *Attorney, Agent, or Firm* — Baker & McKenzie LLP

(57) ABSTRACT

Disclosed embodiments relate to an orthopedic device including a plate and a single-step self-locking mechanism. The plate includes one or more tapered apertures and a slot defined in a top surface of the plate, the slot extending from each aperture. The locking mechanism is slidably seated in the slot and is operable to be positioned in a first position along the slot where a portion of the locking mechanism extends over the aperture or positioned in a second position along the slot where the portion of the locking mechanism is fully retracted from the aperture.

5 Claims, 12 Drawing Sheets

(56) References Cited

U.S. PATENT DOCUMENTS

| | | |
|---|---|---|
| 2005/0059971 A1 | 3/2005 | Michelson |
| 2005/0149026 A1 | 7/2005 | Butler et al. |
| 2007/0083203 A1 | 4/2007 | Ribeiro |
| 2008/0287999 A1 | 11/2008 | Markworth |
| 2009/0012571 A1 | 1/2009 | Perrow et al. |
| 2009/0131988 A1 | 5/2009 | Bush, Jr. et al. |
| 2010/0016901 A1 | 1/2010 | Robinson |
| 2010/0049256 A1 | 2/2010 | Jeon et al. |
| 2010/0069968 A1 | 3/2010 | Assaker et al. |
| 2010/0087871 A1 | 4/2010 | Loyola |
| 2010/0234899 A1 | 9/2010 | Johnson et al. |
| 2011/0029023 A1 | 2/2011 | Tornier |
| 2011/0106159 A1* | 5/2011 | Nazeck .............. A61B 17/7059 606/246 |

* cited by examiner

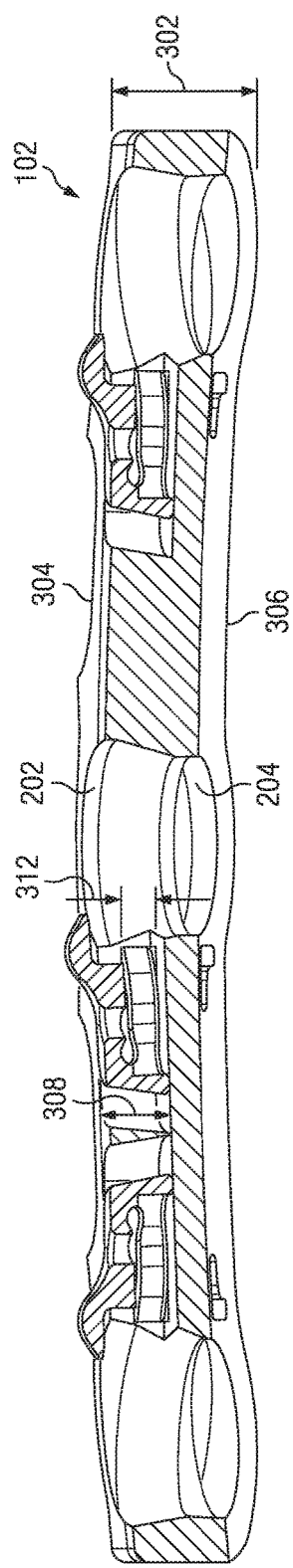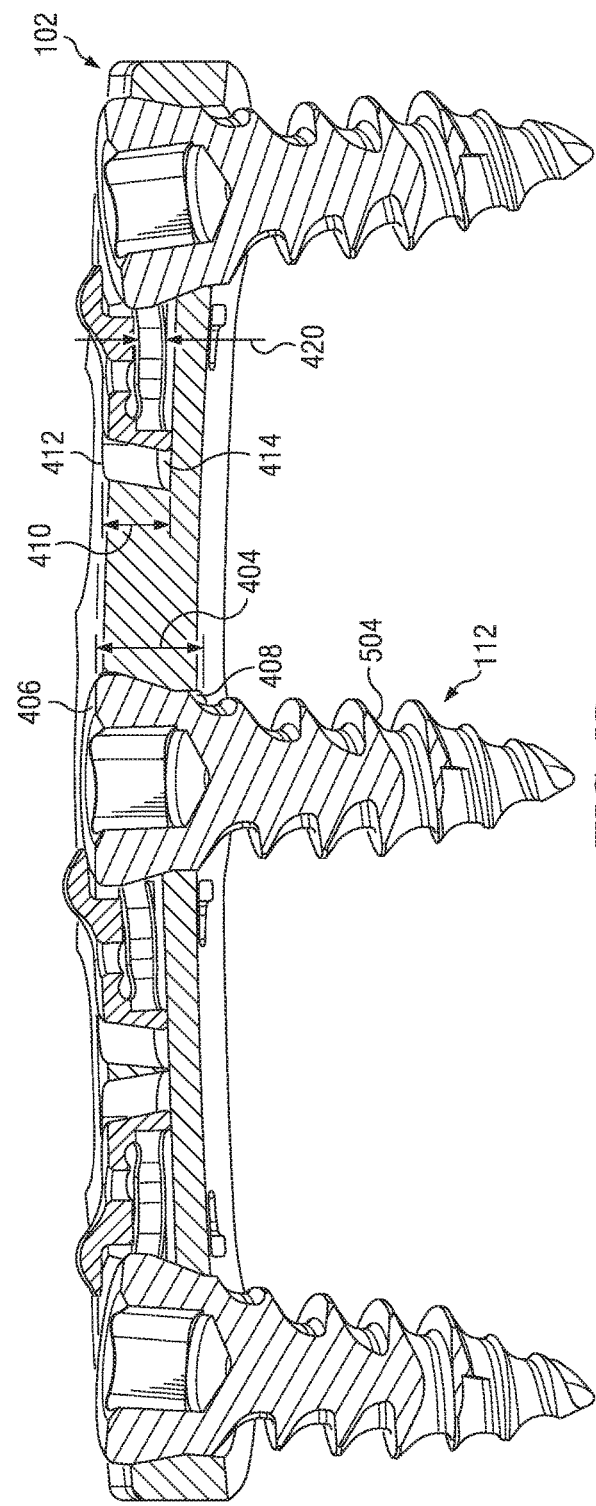
FIG. 5A
FIG. 5B

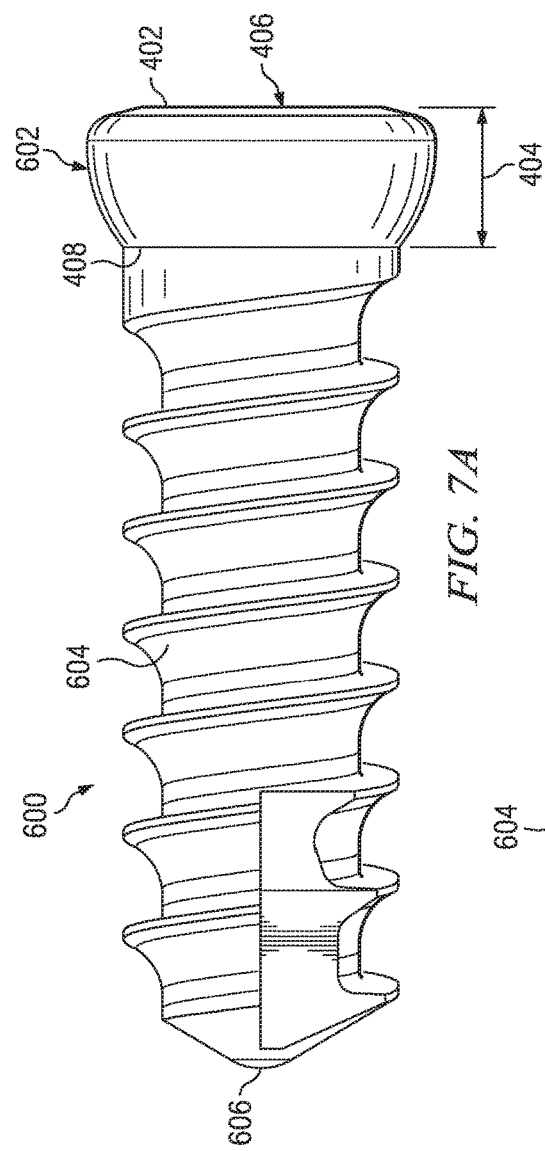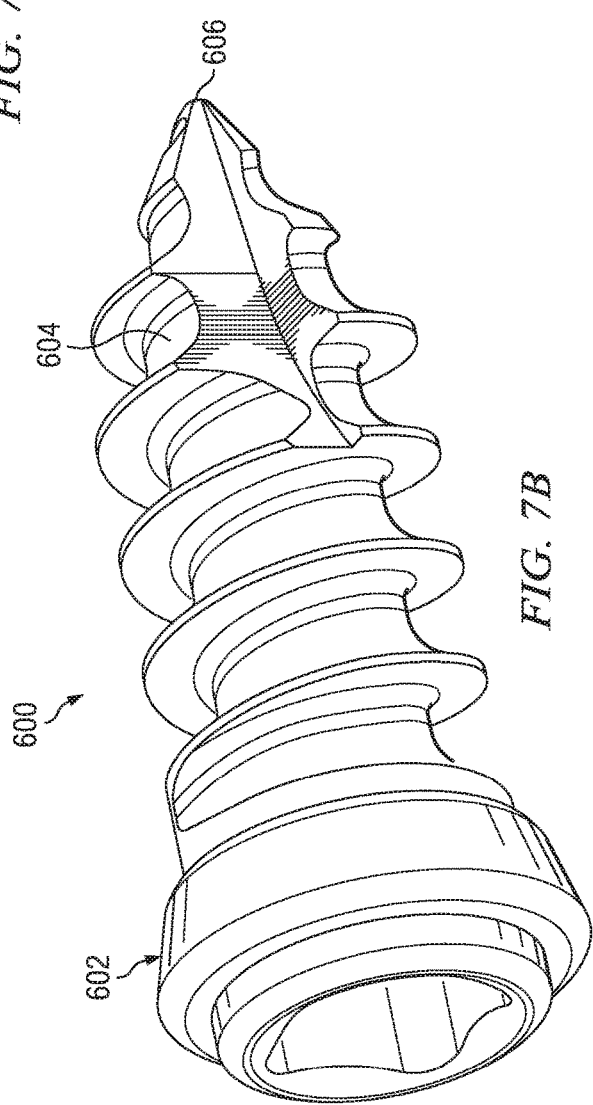

ORTHOPEDIC DEVICES WITH A LOCKING MECHANISM

This is a divisional application of U.S. application Ser. No. 13/489,222, which was filed on Jun. 5, 2012 and is incorporated herein by reference in its entirety.

TECHNICAL FIELD

The disclosed embodiments relate generally to orthopedic devices, and more specifically to self-locking mechanism for retaining a fastener in an orthopedic device.

BACKGROUND

In the human body, the spine generally includes 24 articulate vertebrae and 9 fused vertebrae in the sacrum and the coccyx. The cervical vertebrae are those vertebrae immediately inferior to the skull, located closest to the head and comprise the neck vertebrae. There are seven cervical bones and these bones are, in general, small and delicate. Their spinous processes are short, with the exception of C2 and C7, which have palpable spinous processes. Numbered top-to-bottom from C1-C7, atlas (C1) and axis (C2) are the vertebrae that allow the neck and head so much movement, and therefore are so important for allowing a person to perform day-to-day activities. For the most part, the atlanto-occipital joint allows the skull to move up and down, while the atlanto-axial joint allows the upper neck to twist left and right. The axis also sits upon the first intervertebral disk of the spinal column.

Every year neck pain affects millions of people. Most patients respond well to non-surgical treatments such as medication and physical therapy. However, a small percentage of patients may find nonsurgical interventions fail to relieve the pain. In these patients, symptoms may persist, which may include severe pain, neurologic dysfunction, neck and arm pain, and other symptoms may occur if a cervical intervertebral disc herniates. A disc herniates when some of the disc's gel-like center (the nucleus pulposus) bulges or ruptures through the tough tire-like outer ring (the annulus fibrosus) and presses on nerve roots or the spinal cord. This is called nerve or spinal cord compression.

If surgery is needed to alleviate nerve or spinal cord compression, the surgeon may perform a procedure called an anterior cervical discectomy and fusion. In this procedure, the surgeon makes a small incision in the front (anterior) of the neck to reach the cervical spine. Tissues and muscles are retracted to reveal the proper level in the cervical spine. The disc is removed and the space is filled with bone graft. A cervical plate is then screwed into the superior (top) and inferior (bottom) vertebral bodies, which stabilizes the cervical spine facilitating fusion and healing.

SUMMARY

In accordance with the present disclosure, an embodiment of an orthopedic device comprises a substrate having top and bottom surfaces, an aperture extending from the top surface to the bottom surface, a slot defined in the top surface of the substrate, the slot intersecting the aperture, and a locking mechanism slidably seated in the slot. The locking mechanism may be operable to be positioned in a first position along the slot where an extended portion of the locking mechanism extends over the aperture. The locking mechanism may be further operable to be positioned in a second position along the slot where the extended portion of the locking mechanism is fully retracted from the aperture.

In accordance with the present disclosure, an embodiment of an orthopedic device comprises a substrate having top and bottom surfaces, an aperture extending from the top surface to the bottom surface, a slot defined in the top surface of the substrate, the slot intersecting the aperture, and a locking mechanism slidably seated in the slot. The locking mechanism may be operable to be positioned in a first position along the slot where an extended portion of the locking mechanism extends over the aperture. The locking mechanism may be further operable to be positioned in a second position along the slot where the extended portion of the locking mechanism is fully retracted from the aperture. Additionally, the locking mechanism comprises a pair of compressible flanges received in recess slots defined in sidewalls of the slot; and the extend portion of the locking mechanism comprises a tapered top surface. The tapered top surface may be operable to interact with a fastener as the fastener is being inserted into the aperture longitudinally, the insertion of the fastener operable to cause the locking mechanism to slide laterally along the slot away from the aperture and into the second position.

Also disclosed herein is an exemplary method for preventing a fastener from backing out of an orthopedic device. The method comprises providing an orthopedic device comprising a substrate having top and bottom surfaces, an aperture extending from the top surface to the bottom surface, a slot defined in the top surface of the substrate, the slot intersecting the aperture, and a locking mechanism slidably seated in the slot, the locking mechanism operable to be positioned in a first position along the slot where an extended portion of the locking mechanism extends over the aperture, the locking mechanism further operable to be positioned in a second position along the slot where the extended portion of the locking mechanism is fully retracted from the aperture. The method also includes inserting a fastener into the aperture of the orthopedic device, wherein inserting comprises the fastener interacting with a tapered top surface of the locking mechanism, thereby cause the locking mechanism to slide laterally along the slot away from the aperture and into the second position. The method further includes returning the locking mechanism to the first position after inserting the fastener, whereby an extended portion of the locking mechanism latches against at least a portion of the fastener when a head portion of the fastener is seated in the aperture.

BRIEF DESCRIPTION OF THE DRAWINGS

For a more complete understanding of the present disclosure and its advantages, reference is now made to the following description taken in conjunction with the accompanying drawings, in which like reference numbers indicate like features, and:

FIGS. 5A and 5B illustrate cross-sectional views of the anterior cervical plate shown in FIG. 1 receiving a plurality of fasteners;

FIGS. 7A and 7B illustrate exemplary embodiments of semi-constrained screw fasteners;

DETAILED DESCRIPTION

Cervical plates have been used for more than 20 years to increase neck stability following single and multi-level cervical surgery. These devices improve the success rates of fusion in cervical spine surgery. The stability cervical plates provide may decrease the patient's need to wear a cervical collar post-operatively. However, the screws used to secure the cervical plates to the vertebrae often back out away from the plate, causing pain and discomfort for the patient and preventing the plate from properly stabilizing the neck. Various locking mechanisms are known in the art, but none include a single-step self-locking mechanism that maintains the low profile of the cervical plate. The locking mechanisms known in the art require a surgeon to first move the locking mechanism and then lock the locking mechanism in place.

There is a need for a single-step self-locking mechanism that can be used with an anterior cervical plate to ensure that the screws cannot back out from the plate. Additionally, there is a need for an anterior cervical plate that can receive either constrained or semi-constrained screws without the need for a washer so that surgeons can constrain the screws at one or many orientations. Furthermore, there is a need for a low-profile anterior cervical plate wherein the locking mechanisms and screws do not increase the overall thickness of the plate locking mechanism. Finally, there is a need for a locking mechanism that can be visually inspected post-surgery via fluoroscopy to ensure that the locking mechanism is still in a locked position.

Figure 1A:
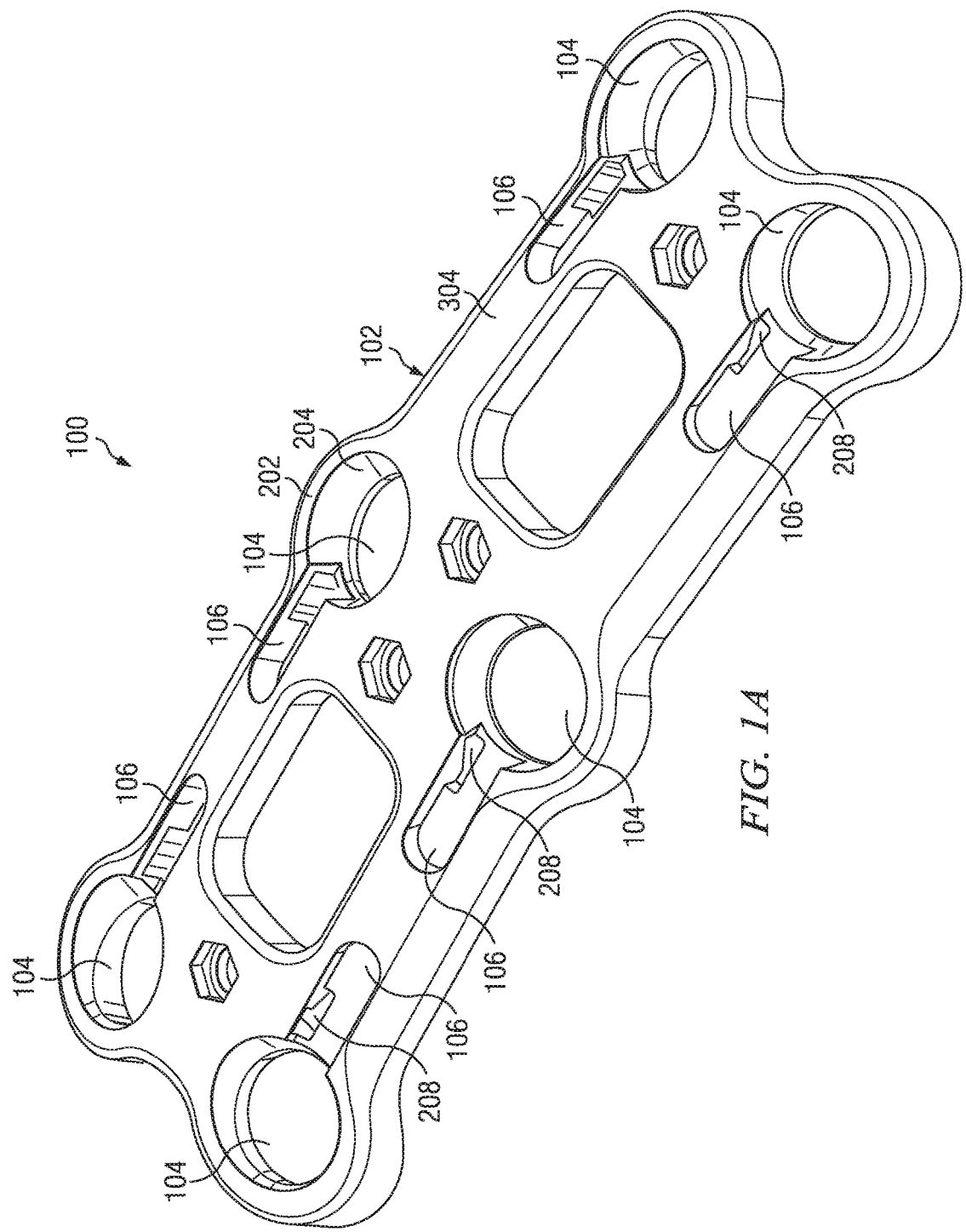
FIGS. 1A-D illustrate an exemplary embodiment of an anterior cervical plate.
Figure 1C:
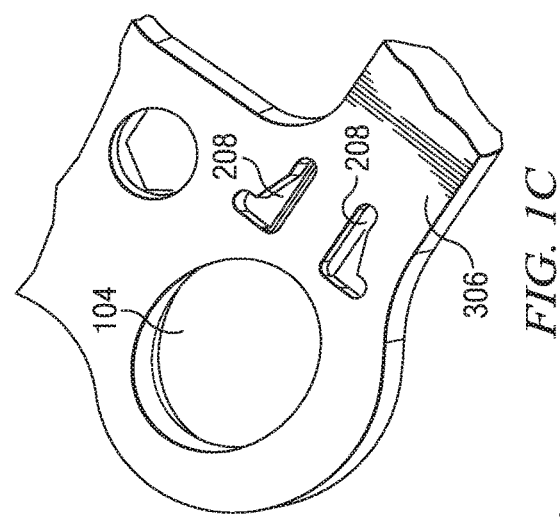
Figure 1B:
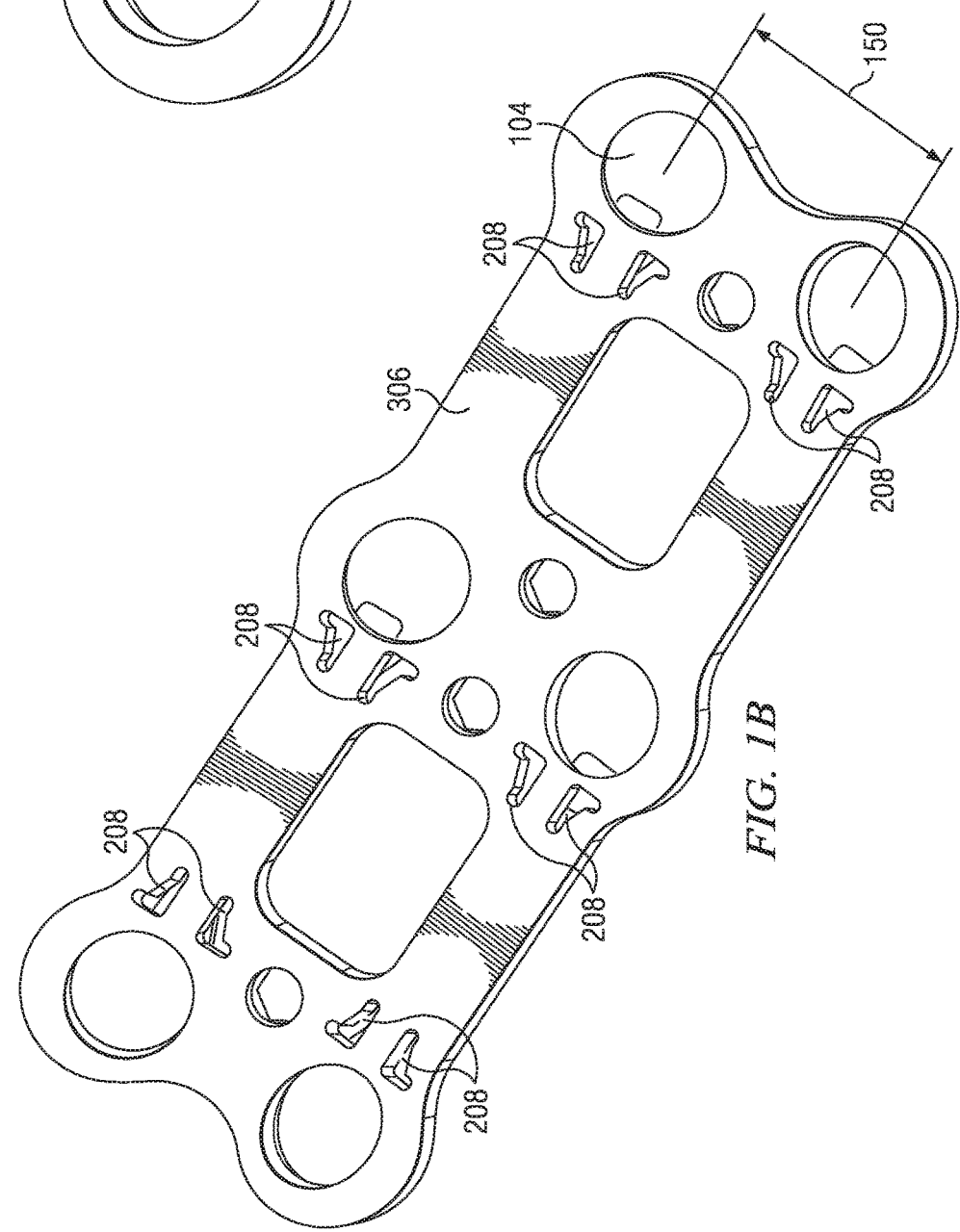

The aforementioned need for a low-profile single-step self-locking mechanism may be satisfied using the embodiments disclosed in this application. FIGS. 1A and 1B illustrate a perspective view and a bottom view of an exemplary embodiment of an anterior cervical plate 100, respectively. FIG. 1C is a partial focused view of the anterior cervical plate 100. The anterior cervical plate 100 comprises a substrate 102 having a tapered aperture 104 extending longitudinally from a top surface 304 of the substrate 102 to a bottom surface 306 of the substrate 102. The substrate 102 further includes a slot 106 defined in the top surface 304 of the substrate 102. The slot 106 extends into the tapered aperture 104 and is configured to receive a locking mechanism 108 slidably disposed therein.

Figure 1D:
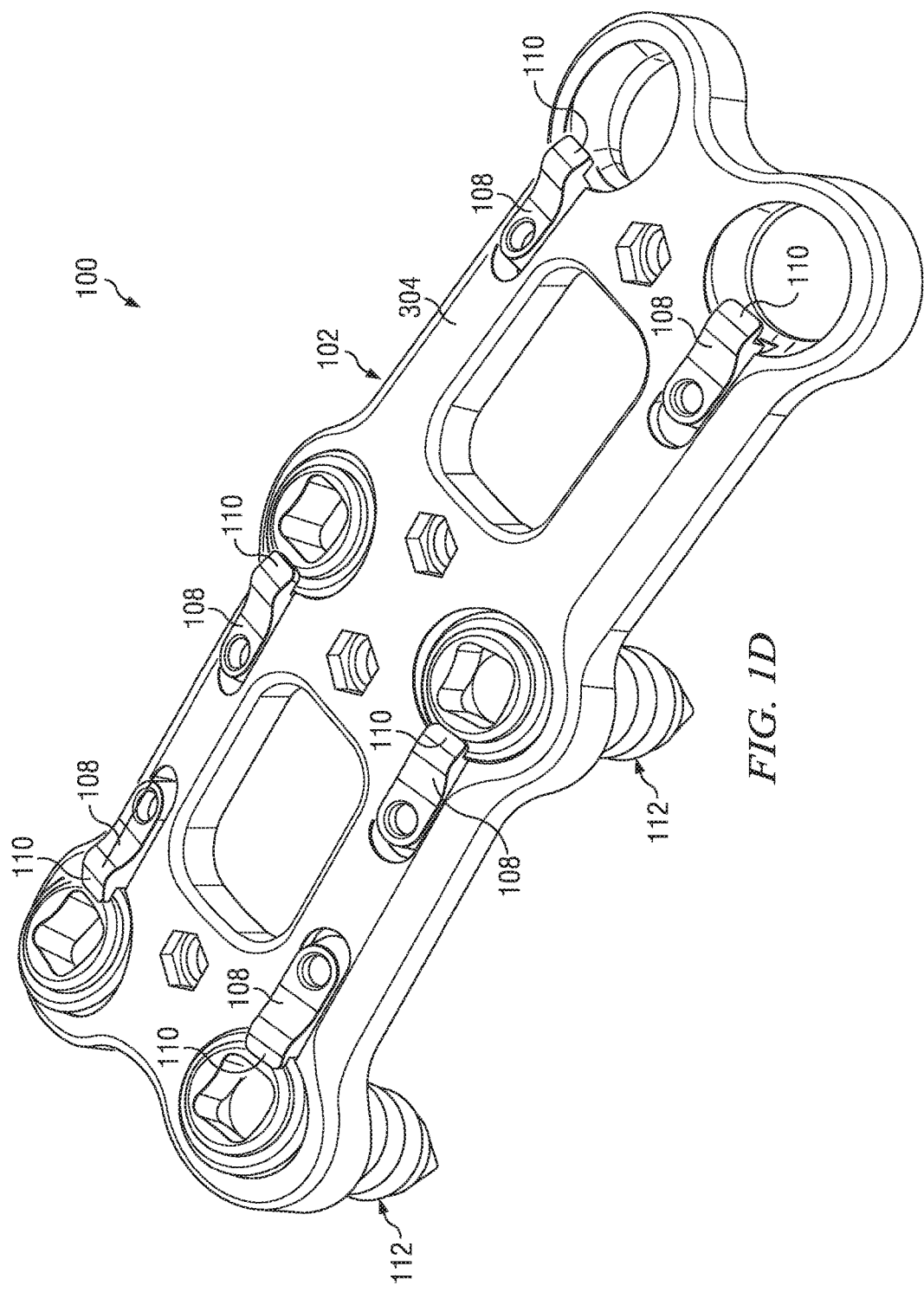

FIG. 1D is a perspective view of the anterior cervical plate 100 comprising fasteners inserted therein. The locking mechanism 108 may be configured to include a tapered top surface 110 that is operable to interact with a fastener 112. In an embodiment, the fastener 112 may comprise a medical screw. In another embodiment, the fastener 112 may comprise any fastening device known in the art.

Figure 2A:
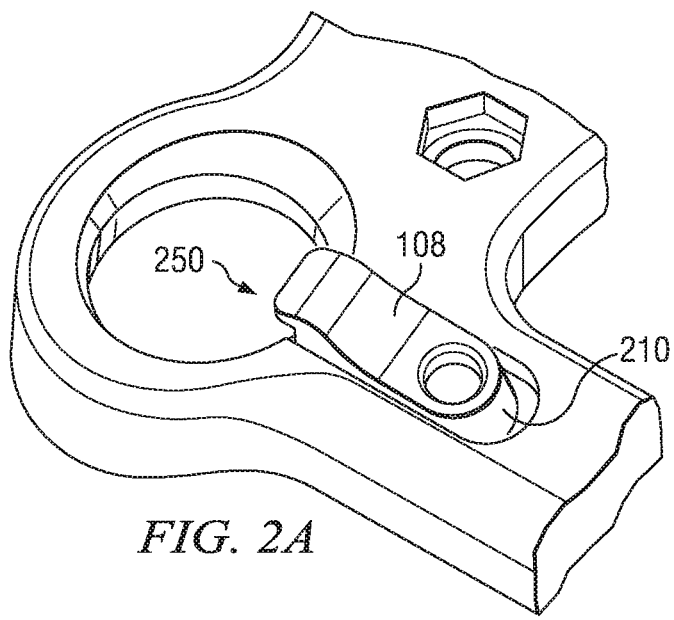
FIGS. 2A and 2B illustrate exemplary positions of a locking mechanism of the anterior cervical plate shown in FIGS. 1A-D.
Figure 2B:
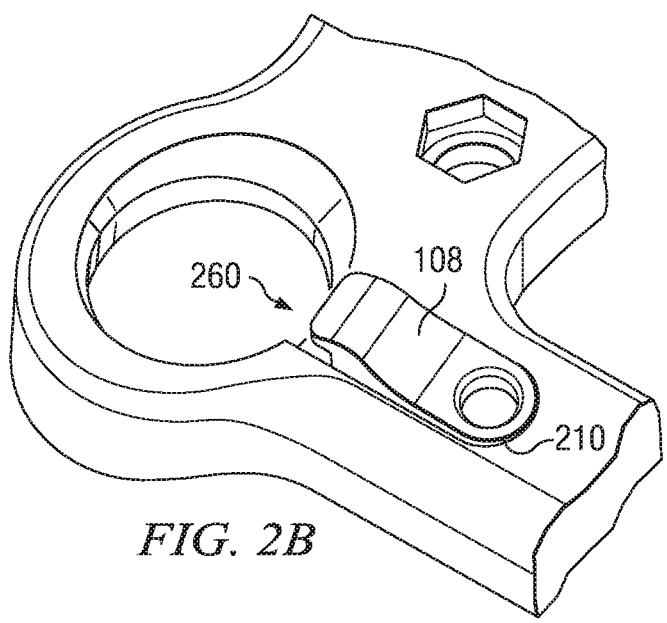

In an embodiment, the locking mechanism 108 may be operable to slide from a first position to a second position along the slot 106. FIG. 2A is a partial focused view of the anterior cervical plate 100 showing the locking mechanism 108 in a first position 250. FIG. 2B is a partial focused view of the anterior cervical plate 100 showing the locking mechanism 108 in a second position 260. In the first position 250, a portion of the locking mechanism 108 may be disposed over the aperture 104. As the fastener 112 is inserted through the tapered aperture 104, the fastener 112 exerts a downward force on the tapered top surface 110 of the locking mechanism 108. The angular alignment of the downward force on the tapered top surface 110 introduces a horizontal force component on the locking mechanism 108 thereby causing the locking mechanism to slide laterally along the slot 106 toward the second position 260.

In an embodiment, as illustrated in FIGS. 1A-D, the substrate 102 may include a plurality of similarly configured tapered apertures 104 defined therein, each adjacent to at least one slot 106 defined in the substrate 102. Further, in an embodiment, as illustrated in FIGS. 1A-D, a plurality of similarly configured locking mechanisms 108 may be slidably disposed in the slots 106 such that at least one locking mechanism 108 is adjacent to each aperture 104. A portion of the at least one locking mechanism 108 is operable to be disposed over the respective aperture 104 depending on the position of the at least one locking mechanism 108.

Referring to FIGS. 1-2, the aperture 104 may have an upper first circumference 202 and a lower second circumference 204. The upper first circumference 202 may be defined on the top surface 304 of the substrate 102, and the lower second circumference 204 may be defined on the bottom surface 306 of the substrate 102. The tapered aperture 104 may extend from the top surface 304 of the substrate 102 through to the bottom surface 306 of the substrate 102. In an embodiment, the lower second circumference 204 may be smaller than the upper first circumference 202. The tapered aperture 104 as configured may thus receive and retain a head of the fastener 112. As described in greater details below, the head of each fastener 112 may have a head width larger than a diameter across the lower second circumference 204, thus allowing the fastener 112 to be seated in the substrate 102 and prevent the fastener 112 from passing all the way through the substrate 102.

Figure 3A:
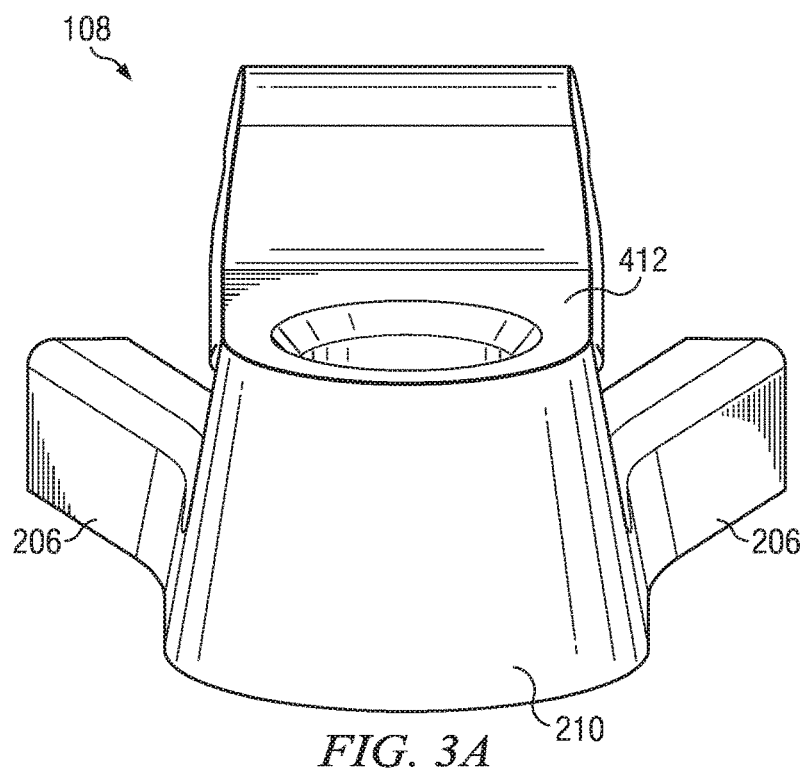
FIGS. 3A and 3B illustrate an exemplary embodiment of the locking mechanism of the anterior cervical plate shown in FIGS. 1A-D.
Figure 3B:
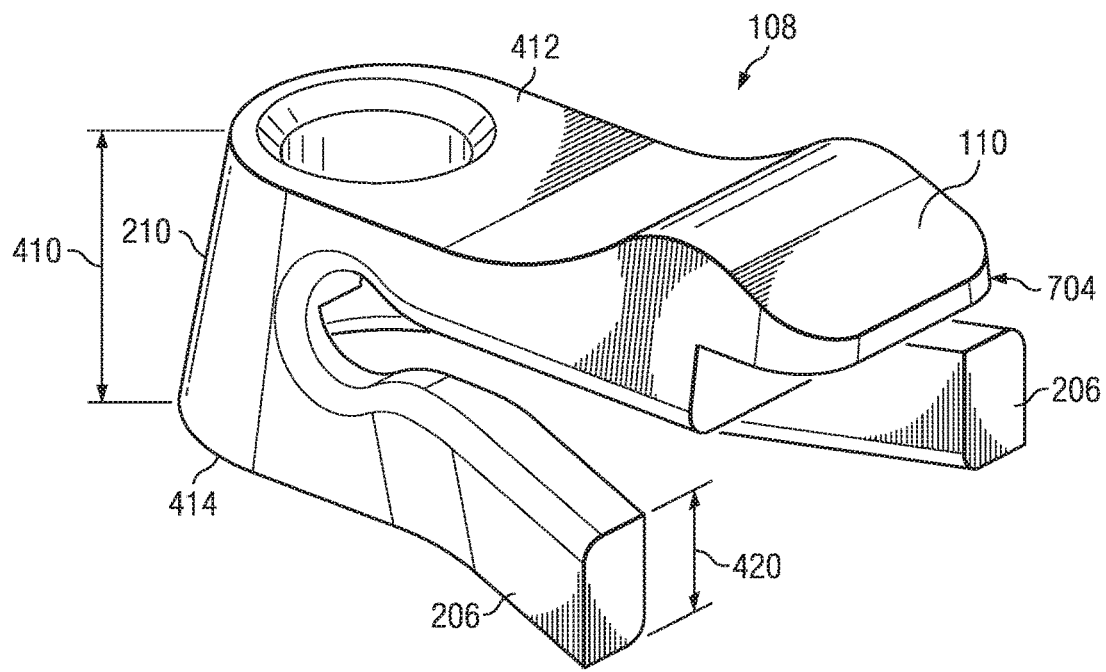

FIGS. 3A and 3B are frontal and perspective views of an exemplary locking mechanism 108, respectively. In an embodiment, the exemplary locking mechanism 108 may include a pair of compressible flanges 206 extending from a base portion 210 of the locking mechanism 108. As illustrated in FIGS. 1-3, flanges 206 of the locking mechanism 108 may be received in angled recessed slots 208 defined in the sidewalls of the slot 106. The flanges 206 may be configured to extend at the same or different angle as the angled recessed slots 208. In an exemplary embodiment, the flanges 206 and the angled recessed slots 208 both may be configured to extend from about 5 to 30 degrees, or more optimally at about 10 degrees, relative to a longitudinal axis of the slot 106. In an embodiment, standard tooling, such as a dovetail cutter (not shown), may be used to manufacture the features of the plate 100, including the angled recessed slots 208. For example, referring to FIGS. 1C-D, small pockets may be milled on the bottom side 306 of the plate to create the angled undercuts for receiving the locking mechanism 108. Other machines, such as sinker EDM, may be used to create the angled recessed slots 208.

Referring to FIGS. 1-3, the structural tension in the flanges 206 may create a natural tendency for them to substantially maintain their relaxed, uncompressed state, and such a tendency to remain uncompressed would drive the locking mechanism 108 to a default position 250 along the slot 106, where the angled recessed slots 208 are wider to allow the flanges 206 to relax and remain uncompressed. In the default position 250, a portion of the locking mechanism 108 may extend over the aperture 104. Referring to FIGS. 1, 2, and 3A-B, when a fastener 112 is inserted longitudinally into a tapered aperture 104, the fastener 112 may interact with the tapered top surface 110 of the respective locking mechanism 108, causing the locking mechanism 108 to slide laterally away from the tapered aperture 104 along the slot 106 and into a retracted position 260 where the locking mechanism 108 is fully retracted from the tapered aperture 104. In the retracted position 260, the flanges 206 of the locking mechanism 108 are compressed against the narrower portion of the angled recessed slots 208.

Figure 4:
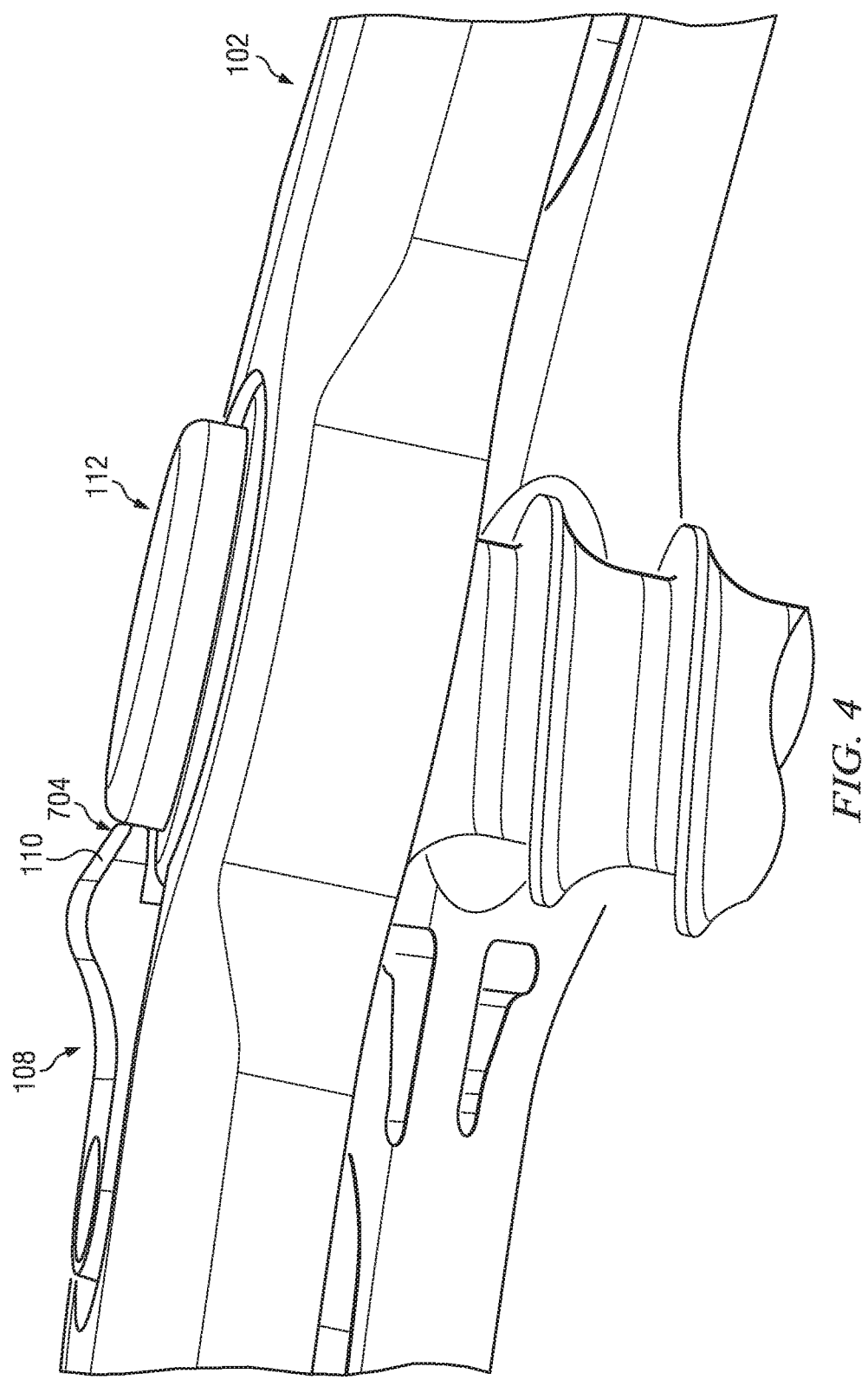
FIG. 4 illustrates a partial focused of the anterior cervical plate shown in FIGS. 1A-D.

When the fastener 112 is seated in the tapered apertures 104 and is no longer interacting with the tapered top surface 100, the compression force of the flanges 206 against the angled recessed slots 208 is operable to push the locking mechanism 108 slidably back towards the default position 250 along the slot 106. Back in the default position 250, the locking mechanism 108 is operable to extend over the tapered apertures 104 above at least a portion of the fastener 112, thus preventing the fasteners 112 from backing out from the substrate 102. FIG. 4 is an illustration of the locking mechanism 108 extending over the aperture 104 to prevent the fastener 112 from backing out.

It is to be appreciated that in an embodiment, the flanges 206 may be replaced with any mechanism that is operable to slide the locking mechanism 108 between the positions 250, 260. For example, an exemplary locking mechanism 108 may be pushed towards the aperture 104 by a spring (not shown) disposed in the recess slot 208. The spring may be machined in to the substrate 102 or modularly disposed therein.

FIG. 5A illustrates a cross-sectional view of the anterior cervical plate 100 shown in FIG. 1. In an embodiment, the substrate 102 of the plate 100 may be configured to have a general thickness corresponding to a first height 302 between the top surface 304 and a bottom surface 306 of the substrate 102. It is to be appreciated that an embodiment of the substrate 102 may have varying thickness or may have a curved profile from one end to another end. The slot 106 may comprise a total depth corresponding to a second height 308 extending from the top surface 304 of the substrate 102 to a bottom surface 310 of the slot 106. As such, the first height 302 is greater than the second height 308. In an embodiment, a height 312 of angled recessed slots 208 may be less than the second height 308, and the angled recessed slots 208 may not extend to the top surface 304 of the substrate 102.

FIG. 5B illustrates a cross-sectional view of the anterior cervical plate 100 shown in FIG. 1 receiving a plurality of fasteners 112. In an exemplary embodiment, the fasteners 112 may comprise medical screws. In an embodiment, each screw 112 may comprise a head 402 which may comprise the same tapering profile as the tapered apertures 104 or other suitable geometric profiles, such a rounded profile. The head 402 of each screw 112 may have a height 404 extending from a top surface 406 of the head 402 to a bottom edge 408 of the head 402. The locking mechanism 108 may have a height 410 extending from a top surface 412 of the locking mechanism 108 to a bottom surface 414 of the locking mechanism 108. The flanges 206 of the locking mechanisms 108 further comprise a height 420 which is less than or equal to the height 308 of the slot 106.

In an embodiment, the height 404 of the head 402 of the screw 112 may be less than or equal to a distance from the bottom surface 310 of the slot 106 to the bottom surface 306 of the substrate 102. Another way to describe the height 404 of the head 402 of the screw 112 is that the height 404 is less than or equal to the difference of the first height 302 of the thickness of the substrate 102 minus the height 302 of the depth of the slot 106.

In an embodiment, the height 410 of the locking mechanism 108 may be less than or equal to the height 308 defined by the depth of the slot 106 from the top surface 304 of the substrate 102 to the bottom surface 310 of the slot 106. The height 410 allows the locking mechanisms 108 to be slidably seated and received within the slot 106 so as not to increase the total height of the anterior cervical plate 100 and to maintain a low-profile nature.

FIG. 5B illustrates the screws 112 being received into the tapered apertures 104 and the respective locking mechanisms 108 in position to prevent the screws 112 from backing out. Initially, as described with respect to FIGS. 1-4, each locking mechanism 108 may operable to be positioned in the first default position 250 as shown in FIG. 2A, so that a portion of the locking mechanism 108 extends over the tapered aperture 104. When a screw 112 is initially received into the tapered aperture 104, the tapered top surface 110 of the locking mechanism 108 interacts with a tip portion of the screw 112, causing the locking mechanism 108 to slide laterally from its first default position 250 to a second retracted position 260 as shown in FIG. 2B. When the locking mechanism 108 is positioned in the second retracted position 260, the flanges 206 are compressed against the angled recess slots 208. Despite the compression force of the flanges 206, which pushes the locking mechanism 108 towards the first position 250, when the screw 112 is inserted into the aperture 104 longitudinally, the force required to torque the screw 112 into the bone (not shown) located below the substrate 102 overcomes the compression force of the flanges 206 and causes the locking mechanism 108 to slide laterally into the second retracted position 260.

While the screw 112 is being inserted into the tapered aperture 104 and driven down towards the bottom surface 306 of the substrate 102, the locking mechanism 108 remains in the second retracted position 260. The screw body 504 keeps the locking mechanism 108 in the second retracted position 260 by preventing the flanges 206 from returning to their relaxed, uncompressed state and sliding the locking mechanism 108 back to the first default position 250.

In an exemplary embodiment, the height 404 of the head 402 is configured such that when the bottom surface 408 of the head 402 reaches the bottom surface 306 of the substrate 102, the head 402 is seated against the surface of the tapered aperture 104, as shown in FIG. 5B. As such, the screw 112 is fully received into the tapered aperture 104, the height 404 of the head 402 fully recesses the head 402 below the depth of the slot 106 defined by the height 308. When the head 402 is fully received, the flanges 206 begin to return to their relaxed state and the locking mechanism 108 is configured to slide laterally within the slot 106 from the second retracted position 260 back to the first default position 250.

In an embodiment, the flanges 206 of the locking mechanism 108 may be configured to cause the locking mechanism 108 to automatically return to the first default position 250 after the fastener 112 clears the locking mechanism 108, eliminating a step required to lock the fastener 112 and reducing the time required in surgery to insert and secure the fasteners 112.

In one embodiment, the anterior cervical plate 100 is configured with six tapered apertures 104 with three in each column in order to fuse two cervical vertebrae. In an embodiment, the substrate 102 may have a width 150 of 5 to 40 mm wide, and more specifically, the substrate 102 may be 10 to 30 mm wide, and optimally, the substrate 102 may be 15 to 20 mm wide. The substrate 102 may be configured to be any length suitable for the intended anatomy, depending on the number of vertebrae that are to be fused together. The substrate 102 may be 1.0 to 4.0 mm thick at the height 302 and the slot 106 may be 0.5 to 3.5 mm deep at the height 308. In an embodiment, the substrate 102 may be 1.5 to 3.0 mm thick at the height 302 and the slot 106 may be 0.75 to 2.5 mm deep at the height 308, and optimally, the substrate 102 may be 1.8 to 2.5 mm thick at the height 302 and the slot 106 may be 0.9 to 2.0 mm deep at the height 308.

The substrate 102 may be made of a variety of materials suitable for the intended anatomical performance parameters. In an exemplary embodiment, the substrate 102 is made from a titanium alloy, although the substrate 102 may also be made from a plastic polymer such as polyether ether ketone (PEEK), stainless steel, or any other known material that is applicable to medical implants.

In an exemplary embodiment, the locking mechanism 108 may be designed to be received in the slot 106 of the substrate 102 so the dimensions of the locking mechanism 108 will match the dimensions of the slot 106. In an exemplary embodiment, the locking mechanism 108 is made from elastic nitinol, which is a nickel titanium alloy, although the locking mechanism 108 may be made from any other material that would allow the flanges 206 to compress slightly when the locking mechanism slides laterally from the first position 250 to the second position 260 and then relax back to their natural, uncompressed state in the first default position 250 after the fastener 112 has passed the locking mechanism 108.

Figure 6A:
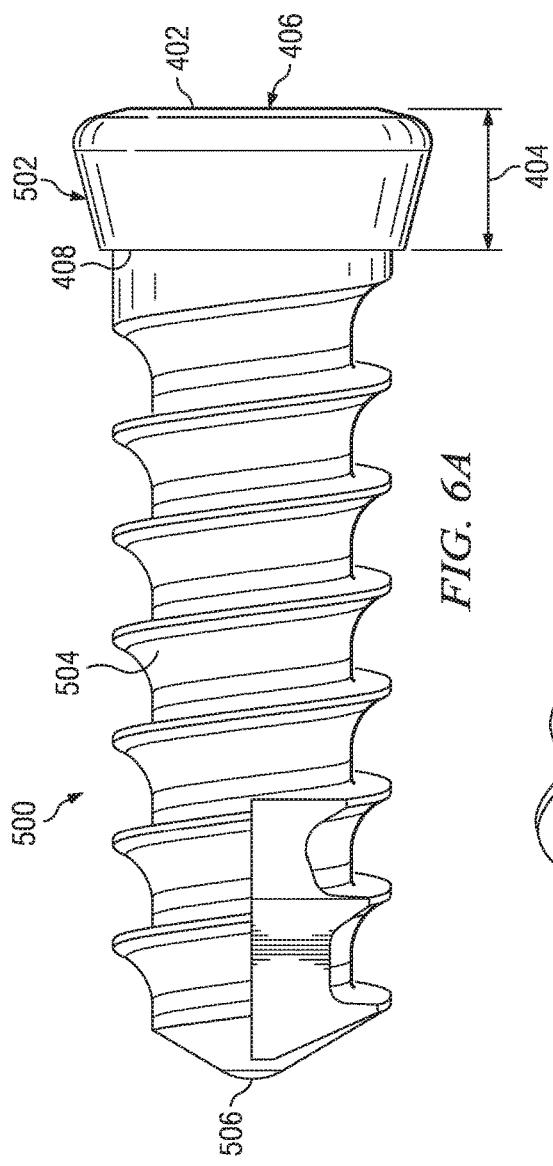
FIGS. 6A and 6B illustrate exemplary embodiments of constrained screw fasteners.
Figure 6B:
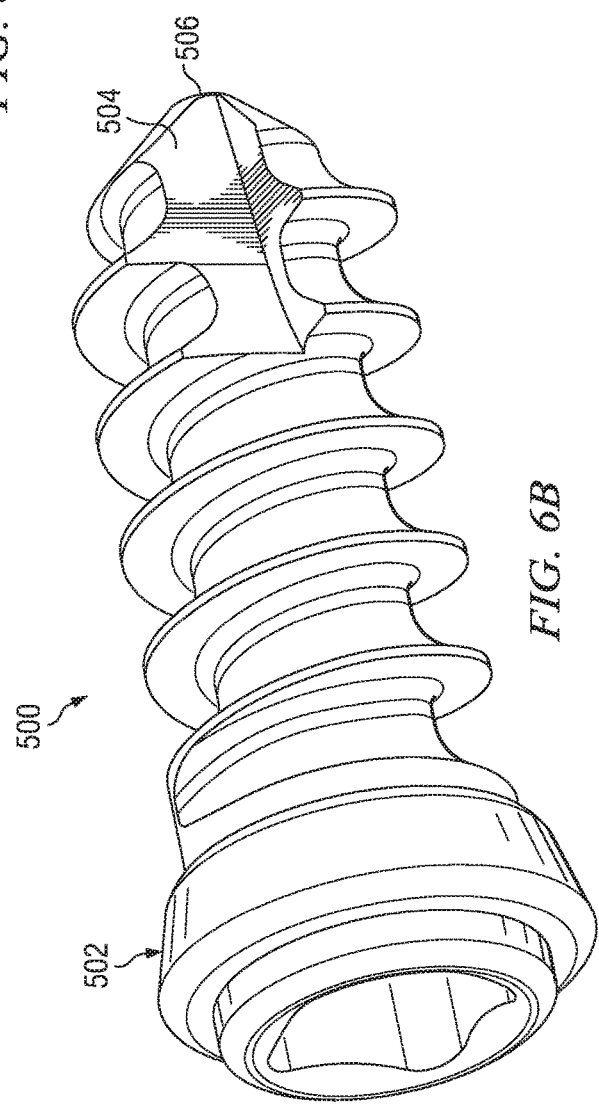

FIGS. 6A and 6B illustrate exemplary embodiments of constrained screw fasteners 500 that may be used in any of the embodiments disclosed herein. The constrained screw fasteners 500 may have a constrained screw head 502, a screw body 504 extending therefrom, and a screw tip 506 at an end of the screw body 504. The screw head 502 may be configured to have any drive feature known in the art, (e.g., square hex, cruciate, etc.) and the screw body 504 may have any screw thread known in the art (e.g., cortical, cancellous, cortico/cancellous, etc.). The screw tip 506 may be configured to have a geometry designed to create either self-tapping or self-drilling screws.

As described with respect FIG. 5B, the height 404 of the constrained screw head 502 is configured to allow the locking mechanism 106 to slide laterally from the second retracted position 260 to the first default position 250 when the constrained screw head 502 is fully received into the tapered aperture 104.

The constrained screw head 502 may have a tapering profile that mates with the corresponding tapering profile of the tapered aperture 104. By having the same tapering profile on the constrained screw head 502 as the tapered aperture 104, the constrained screw fastener 500 may be constrained at one angle. The surgeon installing the cervical plate locking mechanism may be therefore limited to inserting the constrained screw fastener 500 at the angle that matches the taper of tapered aperture 104, but the installation of the cervical plate 100 gains superior strength because the full height of the constrained screw head 502 is mated against the wall of the tapered aperture 104.

FIGS. 7A and 7B illustrate exemplary embodiments of a semi-constrained screw fastener 600. The semi-constrained screw fastener 600 includes a spherical semi-constrained screw head 602, a screw body 604 extending therefrom, and a screw tip 606 at an end portion of the body 604 that may be used in any of the embodiments disclosed herein. As described in FIG. 5B, the height 404 of the spherical semi-constrained screw head 602 is configured to allow the locking mechanism 106 to slide laterally from the second position 418 to the first default position 416 when the spherical semi-constrained screw head 602 is fully received into the tapered aperture 104. The screw head 602 may be configured to have any drive feature known in the art, (e.g., square hex, cruciate, etc.) and the screw body 604 may have any screw thread known in the art (e.g., cortical, cancellous, cortico/cancellous, etc.). The screw tip 606 may be configured to have a geometry designed to create either self-tapping or self-drilling screws.

The spherical semi-constrained screw head 602 has a spherical head that contacts the tapering profile of the tapered aperture 104 at one arc. By having the spherical head on the spherical semi-constrained screw head 602, the semi-constrained screw fastener 600 may be constrained at any angle or orientation within a specified cone of angulation. The specified cone of angulation is such that the spherical semi-constrained screw head 602 maintains adequate contact with the tapered aperture 104, but does not limit the surgeon installing the cervical plate locking mechanism to insert the semi-constrained screw fastener 600 at only one orientation. Therefore, the surgeon is able to install the semi-constrained screw fastener 600 at any orientation within the cone of angulation, giving the surgeon the benefit of ease of installation by not limiting the semi-constrained screw fastener 600 to only one orientation.

Figure 8A:
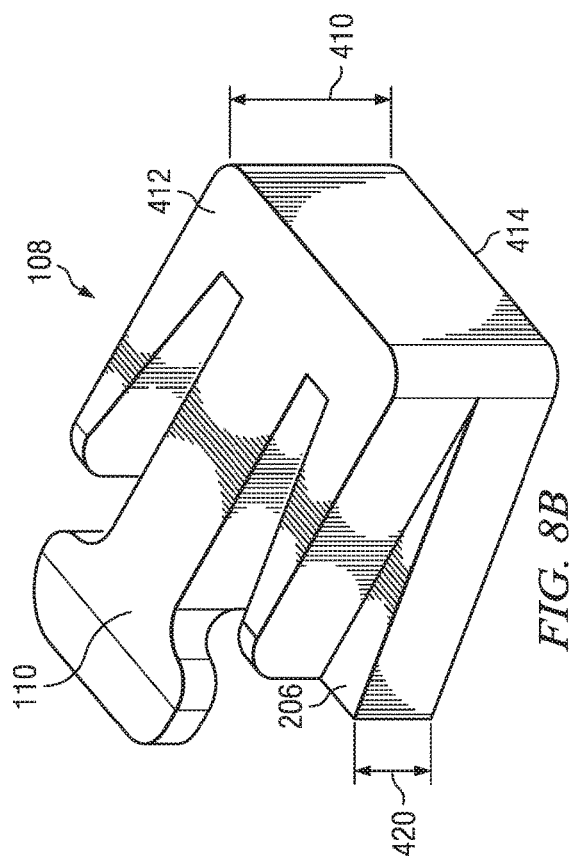
FIGS. 8A and 8B illustrate additional exemplary embodiments of locking mechanisms according to the present disclosure.
Figure 8B:
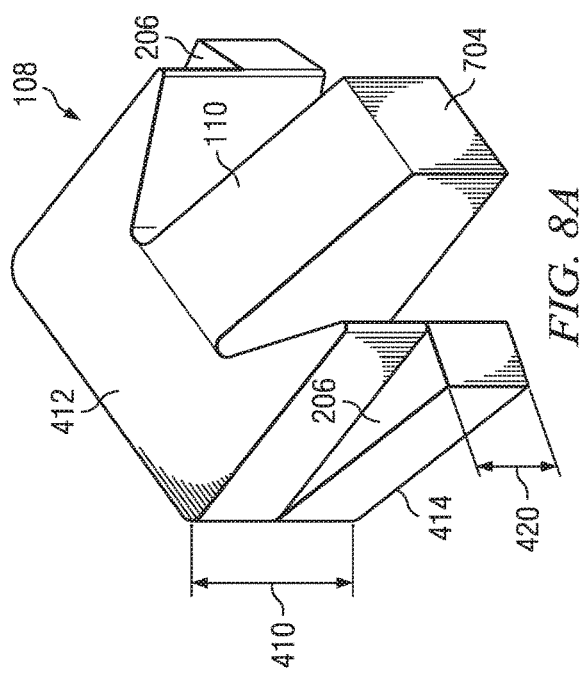

Referring back to FIGS. 3A and 3B, the locking mechanism 108 includes a pair of compressible flanges 206 having an extended portion 704 and a flange height 420. FIGS. 8A and 8B illustrate additional exemplary embodiments of the locking mechanism 108 suitable for the plates of the present disclosure. Referring to the locking mechanism 108 of FIGS. 1-8, the extended portion 704 of the locking mechanism 108, when positioned in the first position 250, extends over the tapered aperture 104. In an exemplary embodiment, only the extended portion 704 extends over the tapered aperture 104 from the slot 106, such that when the fastener 112 is inserted into the tapered aperture 104 longitudinally, the tapered top surface 110 of the extended portion 704 can interact with the fastener 112 to cause the locking mechanism 108 to be able to slide laterally within the slot 106.

As discussed above, the locking mechanism 108 comprises a pair of flanges 206 operable to be received in the angled recessed slots 208 of the slot 106 in the substrate 102. The flanges 206 may extend outwardly from the base portion 210 of the locking mechanism 108. The height 410 is the height of the entire locking mechanism 108 while the winged flange height 420 is less than the height 410 in order to prevent the locking mechanism from being able to be removed from the slot 106 once the locking mechanism 108 is initially received into the slot 106. As discussed above, when the fastener is longitudinally inserted into the tapered aperture 104, the force used to insert the screw compresses the flanges 206 such that the locking mechanism 108 is operable to slide into the second position 260.

Figure 9:
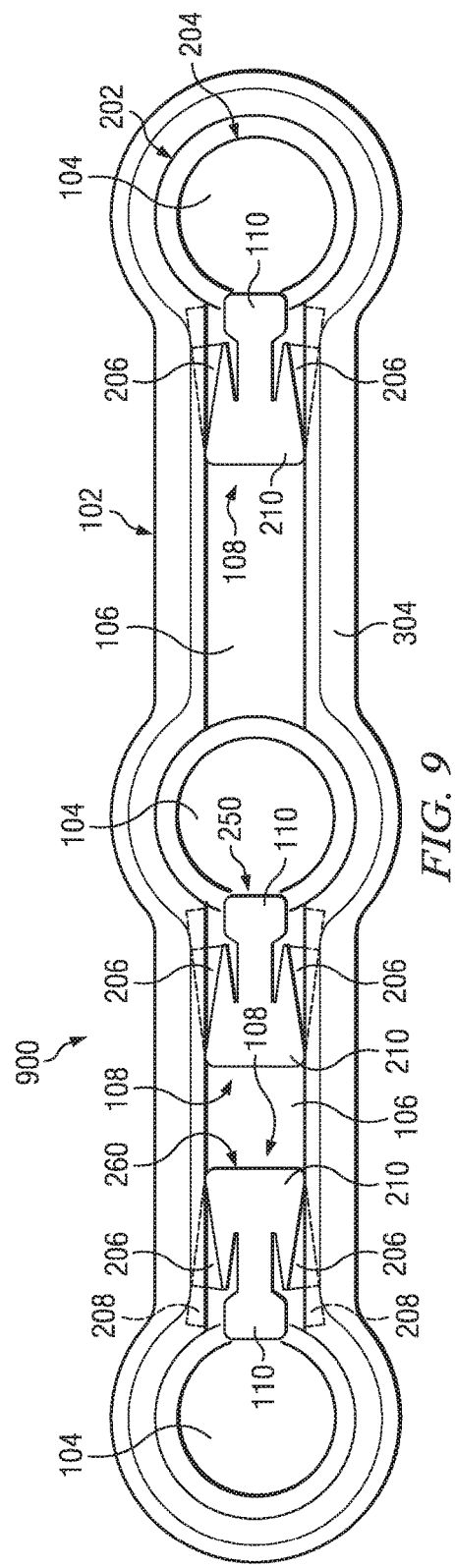
FIG. 9 illustrates another embodiment of an anterior cervical plate.
Figure 10:
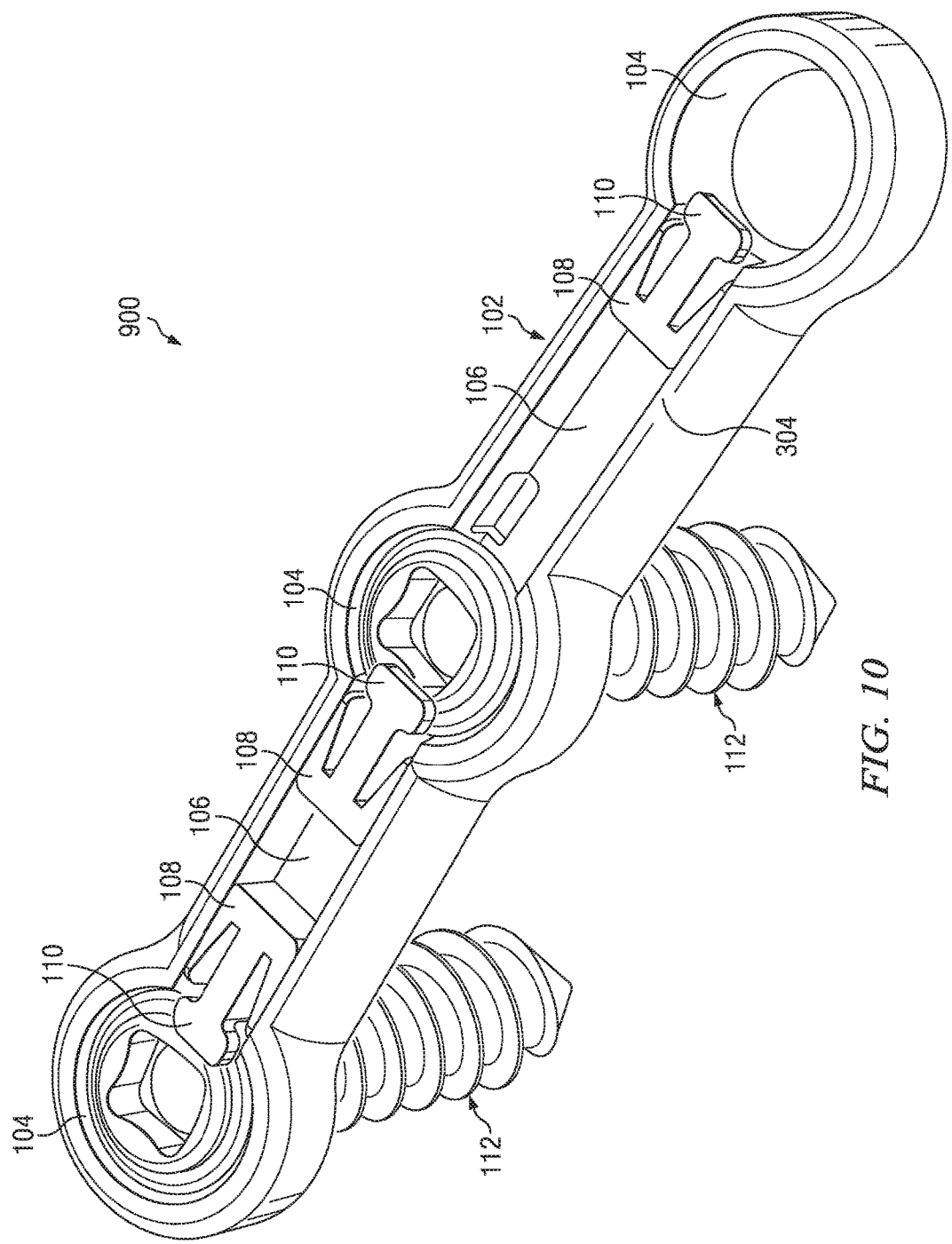
FIG. 10 illustrates a perspective view of the anterior cervical plate shown in FIG. 9 receiving a plurality of fasteners.
Figure 11:
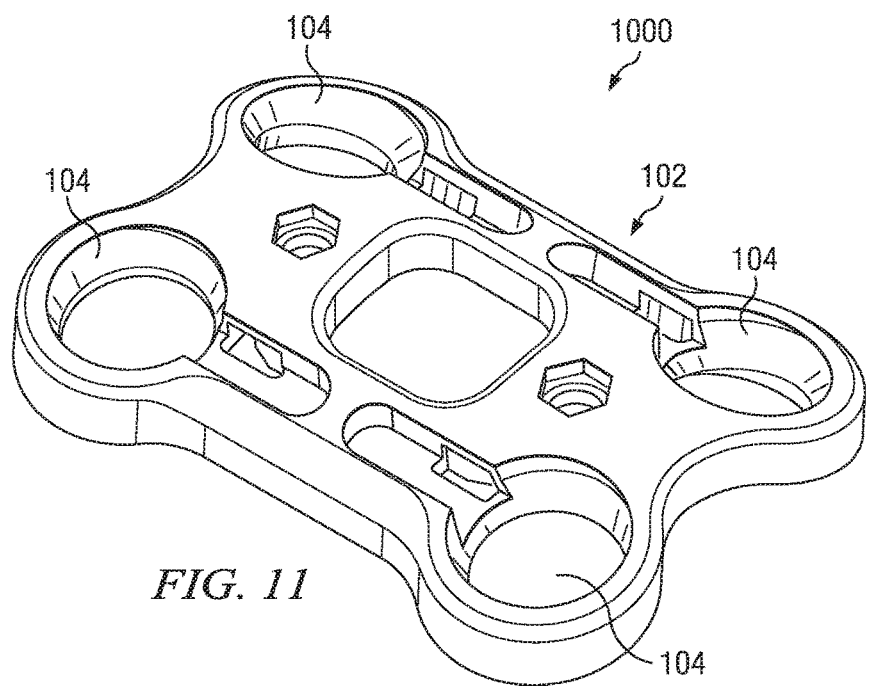
FIG. 11 illustrates yet another embodiment of an anterior cervical plate.
Figure 12:
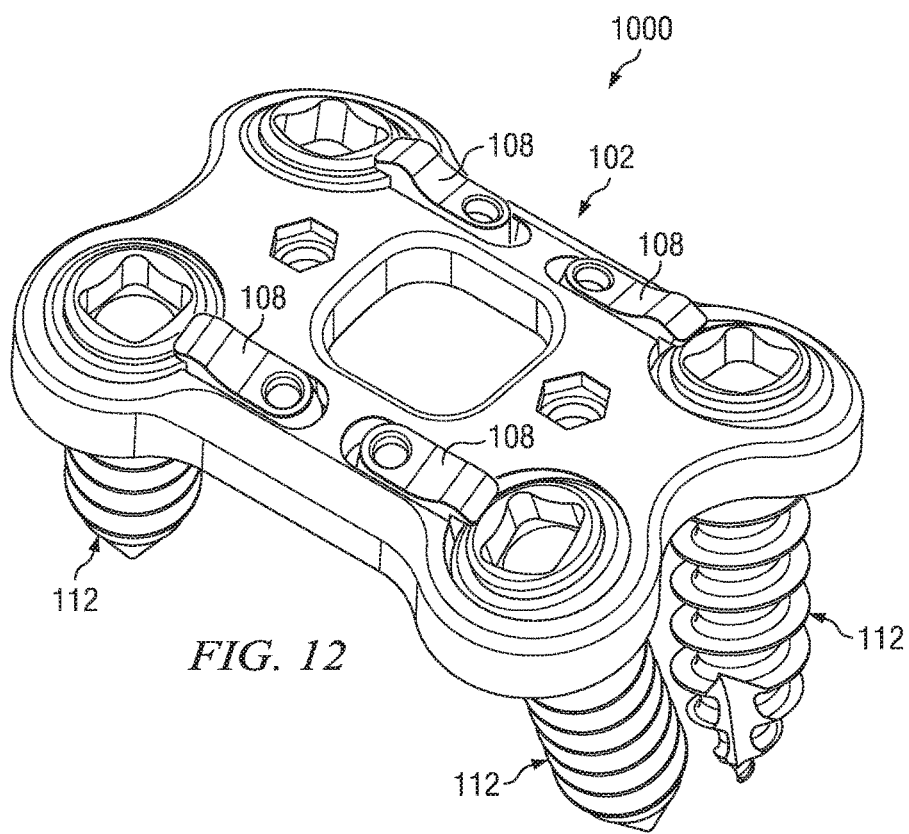
FIG. 12 illustrates a perspective view of the anterior cervical plate shown in FIG. 11 receiving a plurality of fasteners.

The substrate 102 may be configured with any number or spacing of the tapered apertures 104, as needed for a particular surgery or desired by a particular surgeon for his or her patients. FIG. 9 illustrates an embodiment of a unilateral anterior cervical plate 900. FIG. 10 illustrates the unilateral anterior cervical plate 900 shown in FIG. 9 receiving a plurality of fasteners. The anterior cervical plate 900 may be similar to the plate 100 disclosed herein except plate 900 may include three tapered apertures 104 instead of six. In this embodiment, the substrate 102 may be 5 to 10 mm wide, and optimally, the substrate 102 may be about 7 mm wide. FIG. 11 illustrates an embodiment of an anterior cervical plate 1000. FIG. 12 illustrates the unilateral anterior cervical plate 1000 shown in FIG. 11 receiving a plurality of fasteners 112. The anterior cervical plate 1000 may be similar to the plate 100 disclosed herein except plate 1000 may include four apertures 104 with two align in each column.

While various embodiments in accordance with the principles disclosed herein have been described above, it should be understood that they have been presented by way of example only, and not limitation. Thus, the breadth and scope of this disclosure should not be limited by any of the above-described exemplary embodiments, but should be defined only in accordance with any claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 CFR 1.77 or otherwise to provide organizational cues. These headings shall not limit or characterize the embodiment(s) set out in any claims that may issue from this disclosure. Specifically and by way of example, although the headings refer to a "Technical Field," the claims should not be limited by the language chosen under this heading to describe the so-called field. Further, a description of a technology in the "Background" is not to be construed as an admission that certain technology is prior art to any embodiment(s) in this disclosure. Neither is the "Summary" to be considered as a characterization of the embodiment(s) set forth in issued claims. Furthermore, any reference in this disclosure to "invention" in the singular should not be used to argue that there is only a single point of novelty in this disclosure. Multiple embodiments may be set forth according to the limitations of the multiple claims issuing from this disclosure, and such claims accordingly define the embodiment(s), and their equivalents, that are protected thereby. In all instances, the scope of such claims shall be considered on their own merits in light of this disclosure, but should not be constrained by the headings set forth herein.

What is claimed is:

1. A method for preventing a fastener from backing out of an orthopedic device, method comprising:
    providing an orthopedic device comprising:
        a substrate having top and bottom surfaces;
        an aperture extending from the top surface to the bottom surface;
        a slot defined in the top surface of the substrate, the slot intersecting the aperture; and
        a locking mechanism comprising an extended portion and a pair of compressible flanges extending from a base portion, the locking mechanism having a first height at the base and a second height at the pair of compressible flanges, the locking mechanism slidably seated in the slot, the locking mechanism operable to be positioned in a first position along the slot where an extended portion of the locking mechanism extends over the aperture, the locking mechanism further operable to be positioned in a second position along the slot where the extended portion of the locking mechanism is fully retracted from the aperture, wherein the pair of compressible flanges are received in recess slots defined in sidewalls of the slot, and wherein the first height at the base is greater than the second height at the pair of compressible flanges in order to prevent the locking mechanism from being able to be removed from the slot once the locking mechanism is initially received into the slot; and
    inserting a fastener into the aperture of the orthopedic device, wherein inserting comprises the fastener interacting with a tapered top surface of the locking mechanism, thereby cause the locking mechanism to slide laterally along the slot away from the aperture and into the second position; and
    returning the locking mechanism to the first position after inserting the fastener, whereby an extended portion of the locking mechanism latches against at least a portion of the fastener when a head portion of the fastener is seated in the aperture.

2. The method of claim 1, wherein the locking mechanism comprises a pair of compressible flanges received in recess slots defined in sidewalls of the slot, and the pair of compressible flanges are operable to be compressed against the recess slots and exert a horizontal force on the locking mechanism towards the aperture.

3. The method of claim 1, wherein the fastener comprises a semi-constrained screw.

4. The method of claim 1, wherein the fastener comprises a constrained screw.

5. The method of claim 1, wherein the locking mechanism comprises a pair of compressible flanges received in recess slots defined in sidewalls of the slot.

* * * * *